ID#

(12) United States Patent
Cole (10) Patent No.: US 7,871,762 B2
(45) Date of Patent: Jan. 18, 2011

(54) HYPERGLYCOSYLATED HCG (INVASIVE TROPHOBLAST ANTIGEN) IN DIFFERENTIAL DIAGNOSIS OF MALIGNANT OR INVASIVE TROPHOBLASTIC DISEASE

(75) Inventor: Laurence A. Cole, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 1328 days.

(21) Appl. No.: 10/616,323

(22) Filed: Jul. 9, 2003

(65) Prior Publication Data

US 2004/0082020 A1 Apr. 29, 2004

Related U.S. Application Data

(60) Provisional application No. 60/418,128, filed on Oct. 10, 2002.

(51) Int. Cl.
- C12Q 1/00 (2006.01)
- G01N 33/53 (2006.01)
- G01N 33/574 (2006.01)
- C12P 21/08 (2006.01)

(52) U.S. Cl. .................. 435/4; 435/7.1; 435/7.21; 435/7.23; 530/388.1; 530/388.24; 530/388.8; 530/388.85

(58) Field of Classification Search ........... None
See application file for complete search history.

(56) References Cited

U.S. PATENT DOCUMENTS 6,927,034 B2 * 8/2005 O'Connor et al. .......... 435/7.92

OTHER PUBLICATIONS

Cole, LA et al., Prenatal Diagnosis, 1999, 19:351-359.*
Kobata, A, Biochimie, 1988, 70:1575-1585.*
Bowie et al (Science, 1990, 257:1306-1310).*
Burgess et al (J of Cell Bio. 111:2129-2138, 1990).*
Lazar et al (Molecular and Cellular Biology, 1988, 8:1247-1252).*
Birken (Tumor Biology 2005 26:131-141).*
Pandian et al. (Clin. Chem. 2003 49(5): 808-810) teach.*
Cole and Sutton (J. Reproductive Med. 2004 49(7): 545-53).*
Stites et al. (Medical Immunology, 9th Ed, Appleton and Lange, 1997, pp. 250-251).*
Khanlian et al. (American J. of Obstetrics and Gynecology May 2003 188:1254-9).*
Elliott et al, "Carbohydrate and peptide structure of the alpha- and beta-subunits of human chorionic gonadotropin from normal and aberrant pregnancy and choriocarcinoma" *Endocrine* (1997) 7:15-32.
Cole et al.; "Utility of commonly used commercial human chorionic gonadotropin immunoassays in thee diagnosis and management of trophoblastic diseases" *Clinical Chemistry* (2001) 47:308-315.
Cole LA. Phantom hCG and phantom choriocarcinoma. Gynecol Oncol 1998; 71:325-329.

Rotmensch S, Cole LA. False diagnosis and needless therapy of presumed malignant disease in women with false-positive human chorionic gonadotropin concentrations. Lancet 2000; 355:712-715.
Cole LA, Shahabi S, Butler S, Mitchell H, Newlands E, Behrman HR, Verrill HL. Utility of commonly used commercial hCG immunoassays in the diagnosis and management of trophoblastic diseases. Clin Chem 2001; 47:308-315.
Cole LA, Butler SA. False positive or phantom hCG result: a serious problem. Clin Lab Intl 2001; 25:9-14.
Cole LA, Butler SA. Detection of hCG in Trophoblastic Disease: The USA hCG Reference Service experience. J Reprod Med 2002; 47:433-444.
Butler SA, Cole LA. The Use of heterophilic antibody blocking agent (HBT) in reducing false positive hCG results. Clin Chem 2001; 47:1332-1333.
Butler SA, Cole LA. Falsely elevated hCG leading to unnecessary therapy (letter). Obstet Gynecol 99:516-517, 2002.
Cole LA, Shahabi S, Oz UA, Bahado-Singh RO, Mahoney MI. Hyperglycosylated hCG (invasive trophoblast antigen) immunoassay: a new basis for gestational down syndrome screening. Clin Chem 1999; 45:2109-2119.
Suzuki T, Goto S, Nawa A, Kurauchi 0, Saito M, Tomoda Y. Identification of the pregnancy responsible for gestational trophoblastic disease by DNA analysis. Obstet Gynecol 1993:82, 629-34.
Kohorn El. Persistent low-level 'real' human chorionic gonadotropin: a clinical challenge and a therapeutic dilemma. Gynecol Oncol 2002; 85:315-320.
Newlands -ES. Presentation and management of persistent gestational trophoblastic disease and gestational trophoblastic tumors in the UK. In: Hancock BW, Newland ES, Berkowitz RS, editors. Gestational Trophoblastic Disease. London: Chapman and Hall; 1997. p. 143-156.
Berkowitz RS, Goldstein DP. Presentation and management of molar pregnancy. In: Hancock BW, Newland ES, Berkowitz RS, editors. Gestational Trophoblastic Disease. London: Chapman and Hall; 1997. p. 127-142.
O'Connor JF, Ellish N, Kakuma T, Schlatterer J, Kovalevskaya G. Differential urinary gonadotrophin profiles in early pregnancy and early pregnancy loss. Prenat Diagn 1998; 18:1232-1240.
Elliott MM, Kardana A, Lustbader JW, Cole LA. Carbohydrate and peptide structure of the a- and (3-subunits of human chorionic gonadotropin from normal and aberrant pregnancy and choriocarcinoma. Endocrine 7, 15-32, 1997.
Cole LA, Kardana A, Park S-Y, Braunstein GD, "The Deactivation of hCG by Nicking and Dissociation" Journal of Endocrinology and Metabolism 1993; 76:704-710.
Cole LA, "Immunoassay of human chorionic gonadotropin, its free subunits, and metabolites", Clinical Chemistry 1997; 43:2233-2243.
Norman RJ, Buck RH, De Medeiros SF, "Measurement of human chorionic gonadotropin (hCG) :indications and techniques for the clinical laboratory" Ann. Clin. Biochem. 1990; 27:183-194.
Sturgeon CM, McAllister EJ, "Analysis of hCG: clinical applications and assay requirements" Ann. Clin. Biochem. 1998; 35: 460-491.

* cited by examiner

*Primary Examiner*—Peter J Reddig
(74) *Attorney, Agent, or Firm*—Henry D. Coleman; R. Neil Sudol; William J. Sapone (57) ABSTRACT

The invention provides methods for detecting the presence or absence of invasive trophoblast cells. In addition, the invention provides methods for distinguishing quiescent trophoblast diseases from invasive trophoblast diseases and methods for monitoring progression of quiescent trophoblast diseases. The invention provides methods for detecting the presence or absence of germ cell tumors.

13 Claims, 1 Drawing Sheet

Figure 1

HYPERGLYCOSYLATED HCG (INVASIVE TROPHOBLAST ANTIGEN) IN DIFFERENTIAL DIAGNOSIS OF MALIGNANT OR INVASIVE TROPHOBLASTIC DISEASE

This application is related to provisional application Ser. No. 60/418,128 filed Oct. 10, 2002.

FIELD OF THE INVENTION

The invention relates to methods and reagents for differential diagnosis of quiescent and invasive gestational trophoblastic diseases. The invention also relates to methods for detecting the presence or absence of germ cell tumors.

BACKGROUND OF THE INVENTION

A gestational trophoblastic disease is characterized by abnormal cellular growth of the tissues formed as a result of conception, leading to the development of tumors within the uterus. There are three types of gestational trophoblastic tumors: hydatidiform mole/molar pregnancy, choriocarcinoma, and placenta-site trophoblastic tumor (PSTT). Typically, a gestational trophoblastic disease is diagnosed by ultrasound or a Computerized Axial Tomography (CT) or Magnetic Resonance Imaging (MRI) imaging methods. The key test, however, is the hCG blood test.

hCG (human chorionic gonadotropin) is a hormone that increases during pregnancy and is commonly used to confirm pregnancy and as a marker for gestational trophoblastic disease and germ cell tumors. If a woman is not pregnant but has an increased level of hCG it may indicate the presence of a gestational trophoblastic tumor. hCG levels are often rechecked multiple times if a trophoblastic tumor is suspected, since they are a direct measure of the amount of tumor tissue present.

Typically, treatment for gestational trophoblastic disease includes chemotherapy, surgery and combination chemotherapy, or a combination thereof. The treatment or combination of treatments that is recommended will depend upon the severity of the disease. A gestational trophoblastic disease can be invasive, which will require a more rigorous treatment regimen, or non-invasive, which will not require any of the treatments mentioned above. In fact, when non-invasive or slow growing, none of the above mentioned treatments would be effective since they act on fast growing tumors. However, there is currently no accurate method for distinguishing between invasive and non-invasive gestational trophoblastic disease. Thus, there is a need in the art for a method of diagnosing non-invasive gestational trophoblastic disease in order to spare a patient from undergoing unnecessary treatments used to treat invasive gestational trophoblastic disease.

SUMMARY OF THE INVENTION

In one aspect, the invention provides methods for detecting the presence or absence of invasive trophoblast cells comprising the steps of: (a) obtaining a biological sample from a patient; (b) measuring an amount of hCG in the biological sample; (c) measuring an amount of ITA in the biological sample; and (d) determining the percentage of hCG that is ITA, wherein invasive trophoblast cells are detected if the percentage of hCG that is ITA is 30% or greater.

In one embodiment, the patient is a patient in which persistently low hCG titers have been previously detected, and wherein quiescent gestational trophoblastic disease is diagnosed if the percentage of ITA relative to hCG determined in step (d) is less than 30%.

In a further aspect, the invention provides methods for detecting the presence or absence of invasive trophoblast cells in a biological sample comprising the steps of: (a) obtaining a biological sample from a patient; and (b) measuring an amount of ITA in the biological sample; wherein invasive trophoblast cells are detected if the amount of ITA in the biological sample is 2 IU/L or greater.

In another aspect, the invention provides methods for monitoring progression of quiescent gestational trophoblastic disease comprising the steps of: (a) obtaining a biological sample from a patient diagnosed as having quiescent gestational trophoblastic disease; (b) measuring an amount of hCG in the biological sample; (c) repeating steps (a) and (b) with a biological sample obtained at one or more subsequent time points; (d) measuring an amount of ITA in a biological sample obtained in step (c) where the amount of hCG in the biological sample from step (c) is higher than the amount of hCG in step (b); and (e) determining a percentage of hCG that is ITA in the biological sample from step (d).

In yet another aspect, the invention provides methods of detecting the presence or absence of a germ cell tumor in a biological sample comprising the steps of: (a) obtaining a biological sample from a patient; (b) measuring an amount of hCG in the biological sample; (c) measuring an amount of ITA in the biological sample; and (d) determining the percentage of hCG that is ITA, wherein a germ cell tumor is detected if the percentage is 30% or greater.

In a further aspect, the invention provides methods of detecting the presence or absence of a germ cell tumor in a biological sample comprising the steps of: (a) obtaining a biological sample from a patient; and (b) measuring an amount of ITA in the biological sample; wherein a germ cell tumor is detected if the amount of ITA in the biological sample is 2 IU/L or greater.

In another aspect, the invention provides methods of monitoring the progression of a germ cell tumor comprising the steps of: (a) obtaining a biological sample from a patient diagnosed as having a germ cell tumor; (b) measuring an amount of hCG in the biological sample; (c) repeating steps (a) and (b) with a biological sample obtained at subsequent time points; (d) measuring an amount of ITA in a biological sample from step (c) if the amount of hCG in a biological sample from step (c) is higher than the amount of hCG in step (b); and (e) determining the percentage of hCG that is ITA in the biological sample from step (d).

In one embodiment, a germ cell tumor detected or monitored by a method of the invention can be an ovarian germ cell tumor or a testicular germ cell tumor.

Specific preferred embodiments of the present invention will become evident from the following more detailed description of certain preferred embodiments and the claims.

BRIEF DESCRIPTION OF THE DRAWINGS

FIG. 1 is a chart on use of invasive trophoblastic antigen (ITA) as a tumor marker in selected patient populations. Across the X axis: (1) represents the percentages of ITA in 38 patients with persistent low levels of hCG as described in Table 1; (2) represents the percentages of ITA in 4 patients re-referred to the USA hCG Reference Service, all of whom initially presented with persistent low levels of hCG and were either shown or clinically suspected of having malignant gestational trophoblastic disease when sudden rapidly rising hCG levels were detected; and (3) represents 15 other cases with proven gestational trophoblastic disease (choriocarcinoma or invasive placental site trophoblastic tumor). The value 100% indicates that the ITA assay was >99% of that in the total hCG assay (which measures all forms of hCG including ITA). ITA units are equal on a mass basis to hCG units (IU/L).

DESCRIPTION OF THE PREFERRED EMBODIMENTS

As used herein, "hCG" is an abbreviation for human chorionic gonadotropin, a glycoprotein hormone secreted in relatively large quantities by the trophoblast cells of the placenta. The term "intact" or "regular" hCG is used herein to refer to hCG that is composed of two dissimilar subunits, α (92 amino acids and two N-linked oligosaccharides) and β (145 amino acids and two N-linked and four O-linked oligosaccharides), that are joined noncovalently. Both subunits are extensively glycosylated leading to a heterogeneous population of molecular forms. The pattern of glycosylation varies somewhat between sources due to differences in the available processing enzymes. hCG can be detected in the serum and urine of pregnant women and in those with gestational trophoblastic disease.

Free α- and free β-subunits are also detected in serum and urine samples. Both subunits undergo extensive glycosylation, creating a mixture of various forms of hCG and free hCG subunits in a sample. Furthermore, free β subunit and β subunits of intact hCG are frequently cleaved at position 47-48 to produce nicked hCG and nicked β subunit, which are biologically inactive. Further degradation of nicked free β subunit yields a β-core fragment, which forms a large proportion of β subunit-related molecules in urine. For further review of hCG and various forms of hCG, see, for example, Norman et al., 1990, *Ann. Clin. Biochem.* 27:183-194; Cole, 1997, *Clin. Chem.* 43:2233-2243; and Sturgeon et al., 1998, *Ann. Clin. Biochem.* 35:460-491.

As used herein, "ITA" is an abbreviation for invasive trophoblast antigen, also known as hyperglycosylated hCG. ITA is, therefore, a variant of regular hCG, comprising additional side chains of sugars on the N-linked and O-linked sugar chains compared with regular hCG. These additional sugar side chains comprise N-acetylglucosamine, galactose and sialic acid and make the molecule considerably larger in size. ITA is best detected with an immunoassay using the specific monoclonal antibody B152, which only detects ITA. Other methods for detecting ITA include carbohydrate analysis, isoelectric focusing, and the use of lectins, which can distinguish ITA from other forms of hCG based on the carbohydrate units attached to ITA. As discussed herein, ITA is produced by invasive cytotrophoblast cells and malignant germ cells. Typically, measuring ITA levels in a patient who is not pregnant and/or is free of a disease that has cells producing ITA, will yield a background level of ITA of less than 2 IU/L. Thus, as described herein, where a patient is not pregnant, an ITA level of 2 IU/L or greater is indicative of a cancer. In a particular embodiment, where a patient is not pregnant, a level of ITA that is 2 IU/L or greater in a biological sample can indicate the presence of invasive trophoblast cells and/or a germ cell tumor, wherein a level of ITA that is lower than 2 IU/L can indicate the absence of invasive trophoblast cells and/or a germ cell tumor.

The term "hCG" is used herein to refer to any subunit of hCG, fragment of hCG, intact hCG, an isoform of hCG, a modified hCG molecule, total hCG, or any combination thereof. A subunit of hCG can be, for example, α or β subunits. A fragment of hCG can be, for example, β-core fragment or hCG missing the β-subunit C-terminal peptide. A modified hCG molecule can be, for example, nicked free β-subunit or nicked intact hCG. An isoform of hCG can be, for example, ITA.

As used herein, "total hCG" comprises regular hCG and all forms of hCG, including free α and β subunits of hCG and β core fragment of hCG, as well as hCG isoforms such as ITA.

The term "quiescent gestational trophoblastic disease" is used herein to describe a dormant syndrome characterized by non-invasive or quiescent trophoblastic tissue, failed response to chemotherapy and surgery, and the retention of some malignant potential.

The term "gestational trophoblastic disease," as used herein, includes hydatidiform mole/molar pregnancy, choriocarcinoma, and placenta-site trophoblastic tumor.

The term "germ cell" tumor, as used herein, refers to a tumor arising from ovarian germ cells or testicular germ cells. Germ cell tumors that produce ITA include, for example, dysgerminoma and other ovarian germ cell tumors, and testicular choriocarcinoma and seminoma. In one embodiment of the invention, ITA is a useful marker in detecting invasive disease in all these germ cell tumors or malignancies.

The term "biological sample", as used herein, includes, but is not limited to, a quantity of a tissue or body fluid sufficient to measure hCG and/or ITA levels, that is obtained from a mammal. In one embodiment, the mammal is a human. Preferably, a biological sample is urine, saliva, cells, plasma, or serum. Most preferably, a biological sample is urine.

As used herein, the term "patient" includes mammalian subjects. Preferably, a patient is a human. In one embodiment, the patient is a male or female in which persistently low hCG titers have been previously detected, a female diagnosed as having quiescent gestational trophoblastic disease, a female at risk of having or suspected of having a gestational trophoblastic disease, or a male or female at risk of having or suspected of having or in need of screening for a germ cell tumor.

As used herein, a "low level" of hCG is detected where the concentration of hCG is 2 to 200 IU/L. A "persistently" low level of hCG is detected where a low level of hCG is detected in biological samples obtained from a single patient at subsequent time intervals, for example, at weekly, monthly, or bimonthly time intervals.

As used herein, the term "detecting" refers to identifying a patient with invasive trophoblast cells or a germ cell tumor and/or a patient who is at high risk for having an invasive gestational trophoblastic disease or a germ cell tumor.

In one aspect, the invention provides a method of detecting the presence or absence of invasive trophoblast cells comprising the steps of: (a) obtaining a biological sample from a patient; (b) measuring an amount of hCG in the biological sample; (c) measuring an amount of ITA in the biological sample; and (d) determining a percentage of hCG that is ITA, wherein invasive trophoblast cells are detected if the percentage of hCG that is ITA is at least 30%. In one embodiment, the percentage of hCG that is ITA can be at least 35%, 40%, 45%, 50%, 55%, 60%, 65%, 70%, 75%, 80%, 85%, 90%, 95%, or 100%. In a preferred embodiment, invasive trophoblast cells are detected if the percentage of hCG that is ITA is at least 30% or greater. In one embodiment, hCG can be regular hCG, a subunit of hCG, an isoform of hCG, a fragment of hCG, a combination thereof, or total hCG.

Methods for measuring an amount of hCG in a sample are known in the art, and include, for example, using commercially available hCG tests. Such tests have been described, for example, in Cole, 1998, *Gynecol. Oncol.* 71:325-329; Rotmensch et al., 2000, *Lancet* 355:712-715; Cole et al., 2001, Clin. Chem. 47:308-315; Cole et al., 2001, Clin. Lab. Intl. 25:9-14; Cole et al., 2002, J. Reprod. Med. 47:433-444; Butler et al., 2001, Clin. Chem. 47:1332-1333; Butler et al., 2002, Obstet. Gynecol. 99:515-516; Cole et al., 1999, Clin. Chem. 45:2109-2119; all of which are hereby incorporated by reference. The DPC Immulite hCG test (DPC Biermann, Germany) is particularly useful for detecting total hCG.

Methods for measuring an amount of ITA include, for example, methods described in U.S. Pat. No. 6,429,018 (which is hereby incorporated by reference), ITA kits that are available, for example, from Quest Diagnostics (Teterboro, N.J.) and Nichols Institute Diagnostics (San Clemente, Cailf.), and methods described herein.

Any assay that functions to qualitatively or quantitatively determine concentrations of hCG in a biological sample and/or detects ITA concentrations can be employed in the practice of the invention. A direct assay, such as an immunoassay using antibodies that recognize hCG, free hCG subunits, the hCH β-core fragment, and/or specific hCG isoforms, is preferred. Other exemplary assays can involve lectins that assay for carbohydrate moieties, chromatography, chemical or electrophoresis or isoelectric focusing tests that detect glycosylation variants of hCG, and/or antibodies to hyperglycosylated or carbohydrate-variant hCG. Such assays are described in the art.

Immunoassays that can be used to detect hCG or ITA include, but are not limited to, assays employing specific antibodies to hCG or ITA, and assays employing nonspecifically defined antibodies obtained by blind injections of a hCG or ITA into test animals using standard methods. Antibodies to hCG and ITA can be generated by standard means as described, for example, in "Antibodies: A Laboratory Manual" by Harlow and Lane (Cold Spring Harbor Press, 1988), which is hereby incorporated by reference. Any type of fusion phage, monoclonal, or polyclonal antibodies can be used in immunoassays of the invention, so long as the antibodies can be used in a reproducible fashion as markers for hCG or ITA.

In one embodiment, an amount of hCG or ITA can be measured using a capture antibody followed by a labeled secondary antibody using a strategy as described, for example, in U.S. Pat. No. 6,429,018 (which is hereby incorporated by reference). U.S. Pat. No. 6,429,018 teaches the B152 antibody that recognizes ITA but does not detect normal hCG. A labeled secondary antibody useful in a method of the invention can be, for example, an anti-hCG antibody, β-core fragment, α-subunit, and/or β-subunit, providing an assay with polypeptide specificity. The label on the secondary antibody can comprise any chemical, radioactive, lanthanide, colored dye, or genetic tag used in enzyme-linked immunosorbent assays (ELISAs), Western blots, and other sensitive and specific immunoassays and immunoradiometric assays using known methodology. These include conjugating the antibody with horseradish peroxidase or alkaline phosphatase that are easily measurable, typically using colorimetric, fluorometric or luminescent substrates. Genetic labels include firefly luciferase, employed because luciferase produces a bioluminescent molecule when incubated with its substrate, luciferin.

In other embodiments, hCG peptide-specific antibody can be used as a capture antibody, and an antibody specific to ITA can be used as the secondary labeled antibody in an immunoassay such as those described above. Competitive immunoassays can also be used to determine the amount of ITA present among other forms of hCG, including regular and total hCG. For example, an antibody that binds non-specifically to both intact hCG and ITA can be used to immunoprecipitate both forms of hCG present in a sample, followed by a second immunoprecipitation step in which ITA-specific antibodies are used to separate ITA from regular hCG, free hCG subunits, and hCG β core fragment. Isolated ITA protein can then be quantified using standard methods, such as a Bradford protein assay. Alternate embodiments using concanavalin A or other carbohydrate-specific lectin can be used in place of the capture antibody or labeled antibody. Alternatively, prior to an immunoassay, a lectin or chromatographic method can be used to extract ITA from a biological sample. Lectins bind specific carbohydrate structures. Thus, they can be used to differentiate ITA and other forms of hCG, including regular hCG and various hCG subunits or hCG fragments. ITA is also slightly larger than regular hCG and can be separated from regular hCG or other hCG forms by chromatography or electrophoresis.

Carbohydrate analyses include qualitative observations of differences in physical properties between regular hCG and ITA or subunits and fragments thereof, carbohydrate identification using plant lectins specific to the variant carbohydrate portion of ITA obtained by standard lectin screening methods, or any other fingerprinting technique including qualitative or quantitative carbohydrate composition analyses. See, for example, U.S. Pat. No. 6,429,018, which is incorporated by reference.

In certain embodiments, hCG can be purified from biological samples prior to determining the percentage of hCG that is ITA from the sample. Any method for purifying hCG can be used. For example, antibodies specific for hCG can be used to isolate hCG from a biological sample. The amount of ITA in a purified hCG protein fraction can be determined using a method as described above, for example, using an immunoassay with antibodies specific for ITA. ITA specific antibodies are described, for example, in U.S. Pat. No. 6,429,018, which is hereby incorporated by reference. Purified hCG and hCG isoforms from control or test samples can be stored under appropriate conditions, such as those described, for example, in Cole et al, 1999, Clinical Chem. 45:2109-2119, which is hereby incorporated by reference.

One preferred method for determining the amount of ITA in a biological sample is described in U.S. Pat. No. 6,429,018, which teaches a two-step sandwich immunoassay using B152 as capture antibody, and peroxidase labeled monoclonal antibody to hCG β-core, batch 4001 (Genzyme, San Carlos, Calif.) as tracer using the immunoassay methods previously described (Elliott, et al., 1997, Endocrine 7:15-32; and Cole et al., 1993, J. Clin. Endocrinol. Metab. 76:704-710).

In another aspect, the invention provides a method of diagnosing quiescent gestational trophoblastic disease or invasive gestational trophoblastic disease in a patient comprising the steps of: (a) obtaining a biological sample from a patient, wherein the patient has persistently low hCG titers; (b) measuring an amount of hCG in the biological sample; (c) measuring an amount of ITA in the biological sample; and (d) determining the percentage of hCG that is ITA, wherein quiescent gestational trophoblastic disease is diagnosed if the percentage determined in step (d) is less than 30%, and invasive gestational trophoblastic disease is diagnosed if the percentage determined in step (d) is greater than 30%. In one embodiment, hCG can be regular hCG, a subunit of hCG, an isoform of hCG, a fragment of hCG, a combination thereof, or total hCG.

Alternatively, the amount of ITA from step (c) can be compared to a predetermined value, wherein the patient is diagnosed as having invasive gestational trophoblastic disease if the amount of ITA is equal to or greater than the predetermined value, and wherein the patient is diagnosed as having quiescent gestational trophoblastic disease if the amount of ITA is less than the predetermined value. In a particular embodiment, the predetermined value is 2 IU/L, as discussed above. Certain embodiments of this aspect are as defined above, including the definition of patient and persistently low levels of hCG, biological sample, quiescent trophoblastic disease, ITA, and hCG.

As used herein, a "predetermined value" is a standardized value based on a control. For example, a predetermined value can be based on an amount of ITA that is present in a biological sample obtained from a woman previously diagnosed with quiescent gestational trophoblastic disease, i.e. a woman having persistently low hCG levels without a sharp rise in hCG levels. A "persistently low hCG levels" are defined above. A "sharp rise" in hCG levels occurs when an hCG level observed in a biological sample is at least 2 fold greater than an hCG level observed in a biological sample obtained from the same patient at an earlier time point. For example, a sharp rise is observed where hCG levels increase from 5 IU/ml in one biological sample to 10 IU/ml in a subsequently obtained biological sample, wherein the two biological samples were obtained from the same patient.

Alternatively, the "predetermined value" can refer to a value that is based on an amount of ITA in a biological sample obtained from a woman who has confirmed invasive gestational trophoblastic disease, i.e. a woman who has been pathologically diagnosed as having choriocarcinoma. In this embodiment of the invention, the patient is diagnosed as having invasive gestational trophoblastic disease if the amount of ITA is equal to or greater than the predetermined value.

In yet another aspect, the invention provides methods for monitoring the progression of quiescent gestational trophoblastic disease comprising the steps of: (a) obtaining a biological sample from a patient; (b) measuring an amount of hCG in the biological sample; (c) repeating steps (a) and (b) with a biological sample obtained at subsequent time points; (d) measuring an amount of ITA in the biological sample if the amount of hCG in the biological sample from step (c) is higher than the amount of hCG in step (b); and (e) determining the percentage of hCG that is ITA in the biological sample. In one embodiment, the patient can be a patient who was previously diagnosed as having quiescent gestational trophoblastic disease, as diagnosed, for example, using a method of the invention. Alternatively, the patient can be a patient who was previously treated for an invasive gestational trophoblastic disease and whose hCG levels subsequently decreased relative to hCG levels measured prior to treatment for invasive gestational trophoblastic disease. Certain embodiments of this aspect are as defined above, including the definition of patient and persistently low levels of hCG, biological sample, quiescent trophoblastic disease, ITA, and hCG.

In another embodiment, steps (a) and (b) can be repeated, for example, daily, weekly, monthly, bimonthly, every other month, every three months, every four months, every six months, or yearly. In one embodiment, where hCG levels observed over time rise then plateau, quiescent disease is indicated. For example, quiescent disease is indicated where hCG levels rise to 20 IU/ml, then plateau at 22, 18, 25, and 24 IU/ml. Where hCG levels rise consistently or sharply, invasive disease is indicated. For example, invasive disease is indicated where hCG levels rise to 20 IU/ml, then continue to rise to 100 IU/ml then 600 IU/ml. In one embodiment, invasive disease is confirmed in a patient having consistently or sharply rising hCG levels by determining the percentage of ITA relative to the total amount of hCG present in a biological sample from the patient. Where the amount of ITA is at least 30% or higher, invasive disease is diagnosed. In one embodiment, hCG can be regular hCG, a subunit of hCG, an isoform of hCG, a fragment of hCG, a combination thereof, or total hCG.

The methods of the invention can be used to diagnose and/or monitor progression of quiescent gestational trophoblastic disease or invasive gestational trophoblastic disease. One recommended management of quiescent disease is close surveillance without therapy until invasive disease is detected. Specifically, the invention provides the following guidelines for the management and monitoring of quiescent gestational trophoblastic disease.

1. A patient having persistent low levels of serum hCG and/or an ITA amount that is less than 30% of the patient's hCG is given the diagnosis of quiescent gestational trophoblastic disease instead of invasive or malignant gestational trophoblastic disease.
2. Clinicians should refrain from treating quiescent gestational trophoblastic disease cases with chemotherapy, hysterectomy or other surgery.
3. Since quiescent gestational trophoblastic disease cases can develop into an invasive gestational trophoblastic disease, a patient with quiescent gestational trophoblastic disease should be monitored for an abrupt rise in hCG titers, ITA titers, and/or ITA to hCG ratios, which could occur months or years after the detection of persistent low-level hCG titers.

In yet another aspect, the invention provides methods of detecting the presence or absence of a germ cell tumor in a biological sample comprising the steps of: (a) obtaining a biological sample from a patient; (b) measuring an amount of hCG in the biological sample; (c) measuring an amount of ITA in the biological sample; and (d) determining the percentage of hCG that is ITA, wherein a germ cell tumor is detected if the percentage is 30% or greater. In one embodiment, hCG can be regular hCG, a subunit of hCG, an isoform of hCG, a fragment of hCG, a combination thereof, or total hCG.

In a further aspect, the invention provides methods of detecting the presence or absence of a germ cell tumor in a biological sample comprising the steps of: (a) obtaining a biological sample from a patient; and (b) measuring an amount of ITA in the biological sample; wherein a germ cell tumor is detected if the amount of ITA in the biological sample is 2 IU/L or greater.

In another aspect, the invention provides methods of monitoring the progression of a germ cell tumor comprising the steps of: (a) obtaining a biological sample from a patient diagnosed as having a germ cell tumor; (b) measuring an amount of hCG in the biological sample; (c) repeating steps (a) and (b) with a biological sample obtained at subsequent time points; (d) measuring an amount of ITA in a biological sample from step (c) if the amount of hCG in a biological sample from step (c) is higher than the amount of hCG in step (b); and (e) determining the percentage of hCG that is ITA in the biological sample from step (d). In one embodiment, hCG can be regular hCG, a subunit of hCG, an isoform of hCG, a fragment of hCG, a combination thereof, or total hCG.

EXAMPLES

The following example, including the experiments conducted and results achieved is provided for illustrative purposes only and are not to be construed as limiting the invention.

Example 1

ITA Tests Differentiate Quiescent Gestational Trophoblast Disease from Invasive Gestational Trophoblast Disease Samples received in a reference laboratory were initially tested using the automated DPC Immulite total hCG test, the DPC Immulite free hCGβ test, Abbott AxSym total hCG test, and other commercial hCG tests as needed. Serum and urine samples were also analyzed using specialized assays. These included the microtiter plate intact hCG only enzyme immunometric assay, the ITA enzyme immunometric assay, the nicked hCG only enzyme immunometric assay, the free hCG β-subunit only enzyme immunometric assay, and the hCG β-subunit core fragment only enzyme immunometric assay. These specialized tests have been described in detail in previous publications (1-8). Tests were run with and without the Scantibodies, Inc. (San Diego, Cailf.), heterophilic antibody blocking agent to detect substances that falsely elevate hCG titers. Different tests were run as needed, including Sigma Diagnostics (St. Louis, Mo.) urine creatinine test and the automated DPC Immulite LH test (1-8). Clinical reports were prepared from the abbreviated patient history, from the patient's hCG test record, generated data with major commercial automated and "in house" specialized assays, and published data (1-7).

Table 1 outlines the clinical histories provided for the 63 patients with persistent low-level hCG determinations. The table shows the antecedent gestation, the period of persistent low serum hCG results, the limits of serum hCG results as determined by the referring physician's laboratory and the reference laboratory, and therapy used for treating the low hCG results, as indicated in reports to the reference laboratory.

TABLE 1

Histories of 63 Cases with Persistent Low Levels of hCG

| Case | Antecedent Gestation | Period of low serum hCG results | Limits of serum hCG Results | Therapy used after identification of persistent low hCG results |
|---|---|---|---|---|
| 1 | hydatidiform mole | <½ year | 6–37 IU/L | HYS, BSO, EMA-CO, Taxol, Carbo |
| 2 | pregnancy | 2½ year | 13–60 IU/L | Mtx, Act-D, HYS, BSO, EMA-CO |
| 3 | hydatidiform mole | >½ year | 5–10 IU/L | Act-D, Mtx, HYS, EMA-CO |
| 4 | pregnancy | 3 year | 18–150 IU/L | HYS, BSO, Act-D, EMA-CO |
| 5 | pregnancy | 3½ year | 11–19 IU/L | Mtx, Act-D, HYS, BSO, Act-D |
| 6 | hydatidiform mole | 1½ year | <2–39 IU/L | Act-D, EMA-CO, EIP, EIC |
| 7 | pregnancy | 4½ year | 37–198 IU/L (863 IU/L)* | MtxLv, HYS, BSO, Mtx |
| 8 | pregnancy | 6 year | 44–198 IU/L | HYS, Mtx, EMA-CO |
| 9 | hydatidiform mole | unavailable | 100–400 IU/L | HYS, BSO, Act-D |
| 10 | pregnancy | 2 year | <2–90 IU/L | Mtx, Act-D, EMA-CO |
| 11 | pregnancy | 3 year | <1–100 IU/L | Mtx, HYS |
| 12 | hydatidiform mole | 1 year | 6–54 IU/L | HYS |
| 13 | pregnancy | 1 year | 60–130 IU/L | HYS |
| 14 | hydatidiform mole | 3 year | <2–59 IU/L (6000 IU/L)† | BSO, Mtx |
| 15 | hydatidiform mole | <1 year | 2–37 IU/L | Mtx, Mtx, Act-D |
| 16 | hydatidiform mole | <½ year | <5–12 IU/L | Act-D, Mtx |
| 17 | hydatidiform mole | 6 year | 7–35 IU/L | Mtx, Act-D |
| 18 | pregnancy | 2 year | 17–148 IU/L (355 IU/L)‡ | Mtx, Act-D |
| 19 | hydatidiform mole | 1½ year | <2–41 IU/L | Mtx, Act-D |
| 20 | pregnancy | 1 year | 54–500 IU/L | Mtx, Act-D |
| 21 | hydatidiform mole | <½ year | 7–48 IU/L | Mtx, Act-D |
| 22 | pregnancy | <½ year | 7–35 IU/L | Mtx, Mtx |
| 23 | hydatidiform mole | 1 year | 36–66 IU/L | Mtx, Act-D |
| 24 | pregnancy | <½ year | 12–42 IU/L | Mtx, Mtx |
| 25 | hydatidiform mole | <½ year | 7–34 IU/L | Mtx, Act-D |
| 26 | hydatidiform mole | 1½ year | 8–35 IU/L | 5FU |
| 27 | hydatidiform mole | 4½ year | 2–7 IU/L | Act-D |
| 28 | hydatidiform mole | <½ year | 19–32 IU/L | Mtx |
| 29 | pregnancy | <½ year | 165–224 IU/L | Mtx |
| 30 | pregnancy | <½ year | 34–56 IU/L | Mtx |

TABLE 1-continued

Histories of 63 Cases with Persistent Low Levels of hCG

| Case | Antecedent Gestation | Period of low serum hCG results | Limits of serum hCG Results | Therapy used after identification of persistent low hCG results |
|---|---|---|---|---|
| 31 | pregnancy | ½ year | 100–174 IU/L | Mtx |
| 32 | hydatidiform mole | 1 year | 6–13 IU/L | Mtx |
| 33 | pregnancy | <½ year | 10–12 IU/L | Mtx |
| 34 | hydatidiform mole | 1 year | 25–37 IU/L (489 IU/L)§ | Mtx |
| 35 | pregnancy | 2 year | 50–200 IU/L | Mtx |
| 36 | hydatidiform mole | 1 year | 15–33 IU/L | Mtx |
| 37 | pregnancy | 1 year | 2–485 IU/L | chemotherapy, details unavailable |
| 38 | hydatidiform mole | 1 year | <2–23 IU/L | chemotherapy, details unavailable |
| 39 | pregnancy | 2 year | 7–22 IU/L | chemotherapy, details unavailable |
| 40 | hydatidiform mole | 1 year | 8–23 IU/L | chemotherapy, details unavailable |
| 41 | pregnancy | <½ year | 157–206 IU/L | no new or further therapy started |
| 42 | hydatidiform mole | 2½ year | 32–100 IU/L | no new or further therapy started |
| 43 | pregnancy | <½ year | 5–8 IU/L | no new or further therapy started |
| 44 | hydatidiform mole | ½ year | 6–12 IU/L | no new or further therapy started |
| 45 | pregnancy | 1 year | 8–21 IU/L | no new or further therapy started |
| 46 | hydatidiform mole | <½ year | 49–64 IU/L | no new or further therapy started |
| 47 | pregnancy | 3 year | 4–7 IU/L | no new or further therapy started |
| 48 | hydatidiform mole | 1 year | 11–34 IU/L | no new or further therapy started |
| 49 | pregnancy | <½ year | 58–146 IU/L | no new or further therapy started |
| 50 | hydatidiform mole | ½ year | 14–21 IU/L | no new or further therapy started |
| 51 | pregnancy | <1 year | 5–10 IU/L | no new or further therapy started |
| 52 | hydatidiform mole | 1 year | 12–44 IU/L | no new or further therapy started |
| 53 | pregnancy | 2 year | 10–40 IU/L | no new or further therapy started |
| 54 | pregnancy | <½ year | 223–496 IU/L | no new or further therapy started |
| 55 | pregnancy | <½ year | 6–9 IU/L | no new or further therapy started |
| 56 | pregnancy | <½ year | 6–7 IU/L | no new or further therapy started |
| 57 | pregnancy | 5½ year | 23–52 IU/L | no new or further therapy started |
| 58 | pregnancy | <½ year | 8–11 IU/L | no new or further therapy started |
| 59 | pregnancy | <½ year | 3–28 IU/L | no new or further therapy started |
| 60 | GTN | <½ year | <2–57 | no new or further therapy started |
| 61 | pregnancy | <½ year | 10–148 | no new or further therapy started |
| 62 | pregnancy | <½ year | 49–69 IU/L | No new or further therapy started |

TABLE 1-continued

Histories of 63 Cases with Persistent Low Levels of hCG

| Case | Antecedent Gestation | Period of low serum hCG results | Limits of serum hCG Results | Therapy used after identification of persistent low hCG results |
|---|---|---|---|---|
| 63 | pregnancy | <½ year | 13–91 IU/L | No new or further therapy started |

Figure 1:
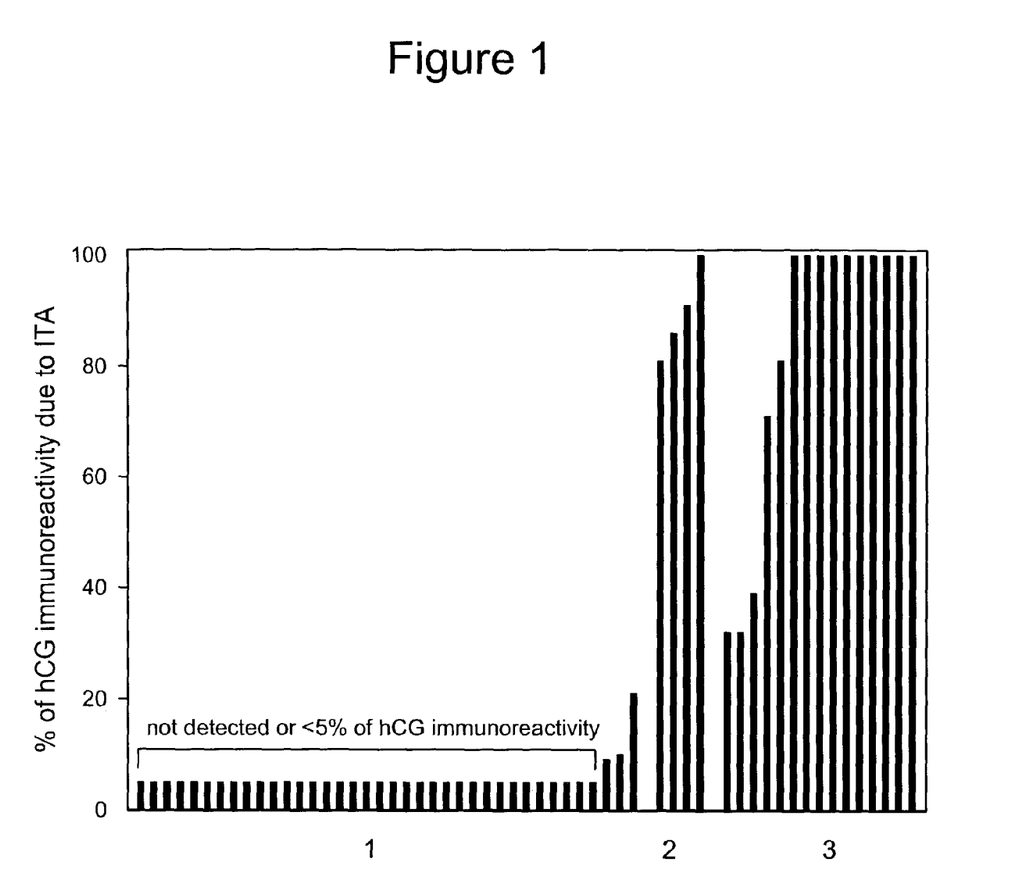

HYS, hysterectomy;
BSO, bilateral salpingoopharectomy;
Carbo, carboplatin;
Mtx, methotrexate;
Act-D, actinomycin D;
EMA-CO, combination etoposide, methotrexate, actinomycin D alternating with cyclophosphamide, and vincristine chemotherapy;
Taxol, paclitaxel;
EIP, combination etoposide, ifosphamide, and cisplatin;
EIC; combination etoposide, ifosphamide, and carboplatin;
MtxLv, methotrexate with leucovorin rescue;
5FU, 5-flurouracil;
Mtx, Mtx, 2 separate treatments with methotrexate;
GTN, gestational trophoblastic neoplasm.
*After 4½ years of persistent low levels (ITA not detected), hCG suddenly rose sharply, and patient was re-referred; hCG was then 863 IU/L, 86% of hCG immunoreactivity due to ITA (FIG. 1). Invasive gestational trophoblastic neoplasm indicated.
†After 3 years of persistent low levels of hCG (ITA not detected) values rose sharply, and patient was re-referred; hCG result was then 6000 IU/L. At this time 81% of hCG immunoreactivity due to ITA (FIG. 1). Invasive gestational trophoblastic neoplasm indicated.
‡After 2 years persistent low levels of hCG results, values sharply increased and patient was re-referred; hCG result was then 355 IU/L. At that time 100% of hCG immunoreactivity due to ITA (FIG. 1); patient was found to have invasive placental trophoblastic tumor.
§After 1 year of persistent low levels of hCG (ITA not detected) values rose sharply, and patient was re-referred; hCG result was then 489 IU/L. At this time 91% of hCG immunoreactivity due to ITA (FIG. 1). Invasive gestational trophoblastic neoplasm indicated.

In all 63 cases, there was no clinical or radiographic evidence of pregnancy or gestational trophoblastic disease or gestational trophoblastic neoplasm. As illustrated, patients with measurable low-level persistent hCG titers were followed for variable time periods (less than 6 months to over 6 years). Intact hCG, free β-subunit, and β-subunit core fragment were measured in serum and urine in all 63 cases. In all cases intact hCG accounted for >90% of combined immunoreactivity. This combination is similar to the normal pregnancy balance of hCG and degradation products. Of note, in 38 (60%) cases, the hCG titers never exceeded 50 IU/L. The clinically recognized pregnancy event before this presentation, referred to in this report as the antecedent pregnancy, was a hydatidiform mole in 27 cases (43%); 35 (56%) had a term, ectopic, or spontaneously aborted pregnancy; one case had a past history of gestational trophoblastic neoplasm.

In all 63 cases, the broad presumptive diagnosis of gestational trophoblastic disease was made, and 40 (64%) underwent single-agent or combination chemotherapy, hysterectomy, or both. Twelve patients underwent hysterectomy and/or bilateral salpingo-oophorectomy, including 10 who also received chemotherapy; 7 received etoposide-based combination chemotherapy; 21 received single-agent methotrexate, or methotrexate with or followed by actinomycin D. Twenty-three cases (37%) received no surgical or chemotherapeutic intervention. Regardless of the therapy provided, in every case, low levels of circulating hCG persisted, and clinically this was perceived as failed therapy. Table 2 outlines a representative case history (case 2 from the Table 1). Of note, this patient had low hCG titers that persisted for at least 2½ years despite aggressive therapy including chemotherapy and hysterectomy.

TABLE 2

Representative case with persistent low levels of serum hCG

| Time (days) | Serum hCG (IU/L) | Notes |
|---|---|---|
| 0 | 44 | incidental pregnancy test |
| 14 | 40 | D&C reveals no evidence of pregnancy |
| 21 | 38 | laparoscopy reveals no ectopic pregnancy |
| 72 | 52 | |
| 79 | 38 | CT/MRI scans reveal no evidence of disease |
| 110 | 40 | |
| 132 | 39 | |
| 177 | 36 | |
| 222 | 30 | CT/MRI scans reveal no evidence of disease |
| 240 | 32 | |
| 267 | 35 | 4 courses of methotrexate chemotherapy |
| 301 | 29 | |
| 322 | 35 | Actinomycin D chemotherapy |
| 346 | 34 | |
| 401 | 28 | |
| 437 | 20 | |
| 467 | 26 | |
| 510 | 24 | |
| 627 | 60 | MRI scan indicates uterine irregularities |
| 632 | 60 | HYS and BSO, pathology unremarkable |
| 642 | 34 | |
| 660 | 13 | |
| 668 | 20 | 3 courses EMA-CO combination therapy |
| 695 | 14 | |
| 740 | 21 | |
| 779 | 20 | |
| 803 | 24 | |

TABLE 2-continued

Representative case with persistent low levels of serum hCG

| Time (days) | Serum hCG (IU/L) | Notes |
|---|---|---|
| 808 | 24 | "real" hCG confirmed ITA not detected indicating the diagnosis of quiescent GTD |

This patient's antecedent gestation was a normal pregnancy (case 2, Table I). hCG levels were measured using commercial available kits at treatment center. Results from the reference laboratory are shown in italics. In this case gestational trophoblastic disease was assumed from the finding of persistent low levels of hCG in the absence of pregnancy.
D&C, dilatation and curettage;
CT, computerized tomographic imaging;
MRI, magnetic resonance imaging;
HYS, hysterectomy;
BSO, bilateral salpingooopharectomy;
EMA-CO, multiagent etoposide, methotrexate, actinomycin D, vincristine, and cyclophosphamide chemotherapy;
ITA, invasive trophoblastic antigen.

In four cases (6.3%), hCG titers abruptly and steeply increased, after prolonged surveillance (after 1, 2, 3, and 4.5 years, respectively) of persistent, low-level hCG titers. In 3 of the 4 cases, the antecedent event was a pregnancy, and in one case was a complete hydatidiform mole. All 4 patients were again referred to the reference laboratory for further evaluation. At this juncture, real hCG titers substantially higher than previous results were demonstrated (Table 1, cases 7, 14, 18 and 34). In one patient tumor was identified in the right lower lobe of the lung by CT imaging. Metastatic placental site trophoblastic tumor was confirmed by pathologic inspection. This patient was given EMA-CO combination chemotherapy (etoposide, methotrexate and actinomycin C alternating with cyclophosphamide and vincristine) without complication. This suppressed the hCG to undetectable levels (<2 IU/L). In the 3 other cases with much higher rising hCG results (489, 865 and 6000 IU/L at time of re-referral), tumor was imaged in the uterus by magnetic imaging in one case. In the other 2 cases CT and magnetic resonance imaging did not identify a tumor. In all 3 cases, considering the rapidly rising hCG, invasive gestational trophoblastic neoplasm or choriocarcinoma was clinically suspected. One of patient was treated with EMA-CO, one with Actinomycin D and the third with methotrexate. In all 3 cases there were no complications and the chemotherapy, at this time, reduced the circulating hCG to undetectable levels.

In addition to intact hCG, free β-subunit and β-subunit core fragment, ITA was also measured in the most recent 38 (60%) cases. In 35 (92%), ITA was either not detectable, or accounted for <5% of hCG immunoreactivity (FIG. 1). This finding indicated the absence of invasive cytotrophoblast cells. The remaining 3 cases were found to have minimal proportions of ITA accounting for 9%, 10% and 21% of total hCG immunoreactivity. In contrast, the 4 patients re-referred to the reference laboratory with rapidly rising hCG titers were found to have high proportions of ITA accounting for 81%, 86%, 91% and 100% of the detected hCG immunoreactivity. In all 4 cases, invasive gestational trophoblastic neoplasm or trophoblastic malignancy was proven or suggested. Because of these findings, the serum from another 15 women with pathologically-confirmed trophoblastic malignancy including invasive placental site trophoblastic tumor (1) and choriocarcinoma (14) were analyzed for the presence of ITA. In 10 (67%), ITA accounted for approximately 100% of the total hCG immunoreactivity, and in all cases, exceeded 30% of the immunoreactivity (FIG. 1). These results indicate that ITA has the sensitivity and specificity to differentiate a pre-invasive form with low hCG titers, or quiescent gestational trophoblastic disease, from malignant or invasive gestational trophoblastic disease.

In all cases, the diagnosis of persistent gestational trophoblastic disease was rendered, although no tumor could be identified by CT or magnetic resonance imaging. Most cases (64%) received single or multi-agent chemotherapy, surgery, or a combination. Despite therapy, measurable circulating hCG persisted. In 38 of 38 cases evaluated by the ITA assay, no or minimal immunoreactivity was identified. This indicated the absence or minimal presence of invasive cytotrophoblastic cells.

Since no discemable tumor was identified, these observations suggest that the persistent low levels of hCG were arising within slow-growing non-invasive trophoblast cells, such as fully differentiated syncytiotrophoblastic cells. It is hypothesized, without wishing to be bound by theory, that fully differentiated syncytiotrophoblastic cells are the source of the persistent hCG, based upon their limited response to chemotherapy, the absence or minimal proportions of ITA, the production of regular intact hCG, and the absence of clinically recognizable tumor. Although these cells have not been specifically identified, presumably they are late pregnancy trophoblast cells that persisted after parturition or evacuation of hydatidiform mole. Recent studies have demonstrated that in some cases the pregnancy associated with the development of gestational trophoblastic disease is not always the one most temporally related (9). In 12 cases, hysterectomy failed to completely suppress circulating hCG, which indicates that some of these cells spread outside the uterus. Although the mechanism is unknown, these cells may have been disseminated by retrograde flow, as has been described for endometriosis. Alternatively, these cells may spread by direct invasion or within lymphatic or vascular spaces, similar to other neoplastic processes involving the mullerian tract. It is further postulated that the presence of persistent quiescent hCG in women with no evidence of clinically detectable tumor constitutes a preinvasive condition that warrants observation without therapy.

In 4 cases, after 1, 2, 3, and 4½ years of dormant gestational trophoblastic disease, there was a consistent steep rise in circulating hCG levels, coincident with the development of invasive gestational trophoblastic disease. These results suggest that these cells retain the propensity to retrodifferentiate or transform into invasive cytotrophoblastic, or cytotrophoblastic-like cells. Of note, all 4 invasive cases were recorded only after re-referral to the reference laboratory. Since there is currently no required follow-up following initial consultation, the number of other cases that subsequently developed malignant disease, but were not referred back, is unknown.

These results indicated that measurement of ITA could distinguish quiescent gestational trophoblastic disease from invasive disease.

Example 2 hCG/ITA Tests in Management of Gestational Trophoblastic Diseases

Forty cases were identified at the USA hCG Reference Service (Albuquerque, N.M.) with low values of real (not false positive) hCG persisting with small variations in hCG results for period ranging from 4 months to 12 years (Table 3). In all cases no tumor was found by ultrasound, CT or MRI scans. In each case persistent gestational trophoblastic disease had been assumed, and in 25 of the 40 cases (63%) referred to the hCG Reference Service (no information available on 2 of the 40 cases) chemotherapy, combination chemotherapy (EMACO) or hysterectomy had been performed. In all cases the therapy failed to completely suppress the hCG values. In all 40 cases real hCG was detected in serum.

TABLE 3

| Case | Time period of persistent low hCG | Limits of variable hCG values over time period | Additional therapy after peristent low hCG results identified |
|---|---|---|---|
| 1 | <½ year | 6–37 IU/L | HYS, SO, EMACO, Taxol, CarP |
| 2 | >½ year | 5–10 IU/L | AcD, Mtx, HYS, EMACO |
| 3 | ? | 100–400 IU/L | HYS, BSO, AcD |
| 4 | 1½ year | <2–39 IU/L | AcD, EMACO, VIP, ICE |
| 7 | 12 years | 3–16 | Mtx, HYS, EMACO |
| 5 | 1½ year | 97–150 IU/L | HYS, Etop |
| 6 | 2 years | 17–48 | Mtx, AcD, HYS |
| 8 | 1 year | 6–54 IU/L | HYS |
| 9 | 6 year | 7–35 IU/L | Mtx, AcD |
| 10 | 1 year | 8–47 IU/L | Mtx, AcD |
| 11 | 1 year | 4–36 IU/L | Mtx, AcD |
| 12 | <½ year | 19–32 IU/L | Mtx |
| 13 | <½ year | <5–12 IU/L | AcD, Mtx |
| 14 | 3 year | <2–59 (6000 IU/L)[1] | BSO, Mtx |
| 15 | 1½ year | <2–41 IU/L | Mtx, AcD |
| 16 | 1 year | 20–56 IU/L | Mtx, AcD |
| 17 | <½ year | 7–48 IU/L | Mtx, AcD |
| 18 | 1 year | 36–66 IU/L | Mtx, AcD |
| 19 | <½ year | 7–34 IU/L | Mtx, AcD |
| 20 | 4½ year | 2–7 IU/L | AcD |
| 21 | 1½ year | 8–35 IU/L | 5FU |
| 22 | 1 year | 6–13 IU/L | Mtx |
| 23 | 1 year | 25–37 IU/L (489 IU/L)[2] | Mtx |
| 24 | 1 year | 15–33 IU/L | Mtx |
| 25 | 2 years | 4–24 IU/L | Mtx |
| 26 | 1 year | <2–23 IU/L | ? |
| 27 | 1 year | 8–23 IU/L | ? |
| 28 | 2½ year | 32–100 IU/L | no further cancer therapy |
| 29 | 1 year | 2–10 IU/L | no further cancer therapy |
| 30 | ½ year | 4–15 IU/L | no further cancer therapy |
| 31 | ½ year | 6–12 IU/L | no further cancer therapy |
| 32 | <½ year | 49–64 IU/L | no further cancer therapy |
| 33 | 1 year | 11–34 IU/L | no further cancer therapy |
| 34 | ½ year | 14–21 IU/L | no further cancer therapy |
| 35 | 1 year | 12–44 IU/L | no further cancer therapy |
| 36 | <½ year | <2–28 (350 IU/L)[3] | no further cancer therapy |
| 37 | <½ year | 5–29 IU/L | no further cancer therapy |
| 38 | 3 year | 94–213 IU/L (213 IU/L)[4] | no further cancer therapy |
| 39 | <0.5 year | <2–57 IU/L | no further cancer therapy |
| 40 | <0.5 year | <2–7 | no further cancer therapy |

[1] After 3 years of persistent low levels of hCG values started to sharply rise. Patient was referred to the USA hCG Reference Service. hCG result was 6000 IU/L. At this time 81% of the total hCG immunoreactivity was shown to be due to hyperglycosylated hCG (Table 4). Malignant disease (gestational trophoblastic disease/choriocarcinoma) was identified and chemotherapy commenced.
[2] After 1 year of persistent low levels of hCG values started to sharply rise. Patient was referred to the USA hCG Reference Service. hCG result was 489 IU/L. At this time 100% of the total hCG immunoreactivity was shown to be due to hyperglycosylated hCG (Table 4). Malignant disease (gestational trophoblastic disease/choriocarcinoma) was indicated and chemotherapy commenced.
[3] A repeat serum and urine sample were requested by the USA hCG Reference Service if hCG results started sharply rising. After 3 months further samples was received, levels rose to 350 IU/L. While on the first occasion, when hCG result was 22 IU/L and no hyperglycosylated hCG was detected. At time of second sample, hCG results was 194 IU/L in our assay and 57% of hCGimmunoreactivity was shown to be due to hyperglycosylated hCG (Table 4). Invasive disease was indicated. Raised hCG was suppressed by EMA-CO chemotherapy.
[4] During 3 years of persistent low levels of hCG, patient was referred to the USA hCG Reference Service twice. On first occasion, after 1 year of persistent low hCG results, hCG result was 44 IU/L and no ITA was detected. At time of second referral, after 3 years of persistent low hCG results, hCG results was 213 IU/L. At this time, however, lung nodule identified by CT scan, and 65% of hCG immunoreactivity was shown to bedue to hyperglycosylated hCG (Table 4). Malignant disease identified and chemotherapy started.

The USA hCG Reference Service found in these cases neither detectable (<2 IU/L) nor significant proportions of ITA, as measured using the Advantage ITA test (Nichols Institute Diagnostics) (<30% of all hCG forms), in serum samples (Table 4). This observation, the lack of clear response to chemotherapy, and the absence of an identifiable mass together suggested that the low levels of hCG may have arisen from spread out, non-invasive cells remaining from a hydatidiform mole or other source of trophoblast cells. It was inferred that the pregnancy-like hCG produced by scattered differentiated trophoblast cells remaining from evacuation of hydatidiform mole or other source of trophoblast cells, were non-invasive cells, and that because they were slow growing, did not respond to chemotherapy.

TABLE 4

| Total serum hCG immunoreactivity IU/L | Hyperglycosylated hCG Percentage of total hCG immunoreactivity |
|---|---|
| A. Cases with persistent low levels of hCG | |
| 38 | Not detected (<2 IU/L) |
| 50 | Not detected (<2 IU/L) |
| 14 | Not detected (<2 IU/L) |

TABLE 4-continued

| Total serum hCG immunoreactivity IU/L | Hyperglycosylated hCG Percentage of total hCG immunoreactivity |
|---|---|
| 16 | Not detected (<2 IU/L) |
| 22 | Not detected (<2 IU/L) |
| 22 | Not detected (<2 IU/L) |
| 13 | Not detected (<2 IU/L) |
| 34 | Not detected (<2 IU/L) |
| 56 | Not detected (<2 IU/L) |
| 39 | Not detected (<2 IU/L) |
| 213 | Not detected (<2 IU/L) |
| 57 | Not detected (<2 IU/L) |
| 148 | Not detected (<2 IU/L) |
| 224 | Not detected (<2 IU/L) |
| 496 | Not detected (<2 IU/L) |
| 12 | Not detected (<2 IU/L) |
| 21 | Not detected (<2 IU/L) |
| 20 | Not detected (<2 IU/L) |
| 100 | Not detected (<2 IU/L) |
| 7 | Not detected (<2 IU/L) |
| 150 | Not detected (<2 IU/L) |
| 20 | Not detected (<2 IU/L) |
| 21 | Not detected (<2 IU/L) |
| 37 | Not detected (<2 IU/L) |
| 47 | Not detected (<2 IU/L) |
| 48 | Not detected (<2 IU/L) |
| 130 | Not detected (<2 IU/L) |
| 29 | Not detected (<2 IU/L) |
| 24 | Not detected (<2 IU/L) |
| 7.7 | Not detected (<2 IU/L) |
| 10.6 | Not detected (<2 IU/L) |
| 88 | Not detected (<2 IU/L) |
| 42 | Not detected (<2 IU/L) |
| 24 | Not detected (<2 IU/L) |
| 16 | Not detected (<2 IU/L) |
| 51 | Not detected (<2 IU/L) |
| 16.5 | Not detected (<2 IU/L) |
| 74 | Not detected (<2 IU/L) |
| 90 | Not detected (<2 IU/L) |
| 9.8 | Not detected (<2 IU/L) |
| 8 | Not detected (<2 IU/L) |
| 44 | Not detected (<2 IU/L) |
| 60 | Not detected (<2 IU/L) |
| 12 | Not detected (<2 IU/L) |
| 35 | Not detected (<2 IU/L) |
| 11 | Not detected (<2 IU/L) |
| 5.9 | Not detected (<2 IU/L) |
| 35 | Not detected (<2 IU/L) |
| 35 | Not detected (<2 IU/L) |
| 750 | 3.9% |
| 198 | 9.1% |
| 212 | 10% |
| 23 | 21% |
| B. Cases with proven malignant/invasive trophoblastic disease | |
| 2450 | 32% |
| 19950 | 32% |
| 8130 | 39% |
| 330 | 71% |
| 670 | ~100% |
| 2000 | ~100% |
| 2500 | ~100% |
| 5000 | ~100% |
| 37500 | ~100% |
| 38700 | ~100% |
| 45000 | ~100% |
| 90000 | ~100% |
| 131250 | ~100% |
| C. Cases with history of persistent low hCG that developed malignant/invasive disease | |
| 6000 | 81%[1] |
| 489 | 100%[1] |
| 350 | 57%[1] |
| 213 | 65%[2] |
| 863 | 86%[2] |
| 190 | 100%[2] |
| 1255 | 100%[2] |

[1] Those with past history of gestational trophoblastic disease (Table 3 cases 13, 22, 35, 37).
[2] Those with no past history of gestational trophoblastic disease (Table 5 cases 4, 11, 19).

In one of the 26 cases (case 14 in Table 3), after 3 years of low levels of hCG, hCG values sharply rose. The patient was referred again to the USA hCG Reference Service. The hCG result was 6000 IU/L. At this time 81% of the total hCG immunoreactivity was shown to be due to ITA (Table 4), consistent with invasive/malignant disease. A CT scan detected a tumor, gestational trophoblastic disease/choriocarcinoma was diagnosed and EMA-CO chemotherapy was started. As described in Table 3, three other cases (23, 36 and 38) had rising hCG results and invasive disease, accompanied by ITA to total hCG ratios of 100%, 57%, and 65%, respectively.

The USA hCG Reference service also consulted on 40 other cases with persistent low hCG values but with history of pregnancy and no history of trophoblastic diseases whatsoever (Table 5). In these cases, persistent low hCG levels were detected from 2 month to 6 years. In all 40 cases hCG was identified in both serum and urine samples. The hCG resembled normal second or third trimester pregnancy hCG, with very little or no ITA (<2 IU/L or <30% of total hCG). In all 40 cases no tumor mass was identified. Little or no response was observed to chemotherapy.

TABLE 5

| Case | Time period of persistent low hCG | Limits of variable hCG values over time period | Therapy |
|---|---|---|---|
| 1 | 3 year | 13–60 IU/L | Mtx, AcD, HYS, BSO, EMACO |
| 2 | 3 year | 18–150 IU/L | HYS, BSO, AcD, EMACO |
| 3 | 3½ year | 11–19 IU/L | Mtx, AcD, HYS, BSO, AcD |
| 4 | 4 year | 37–198 IU/L (863 IU/L)[1] | MtxLv, HYS, BSO, Mtx |
| 5 | 6 year | 44–198 IU/L | HYS, Mtx, EMACO |
| 6 | 2 year | <2–90 IU/L | Mtx, AcD, EMACO |
| 7 | 2 years | 5–130 IU/L | Mtx, AcD, HYS |
| 8 | 3 year | <1–100 IU/L | Mtx, HYS |

TABLE 5-continued

| Case | Time period of persistent low hCG | Limits of variable hCG values over time period | Therapy |
|---|---|---|---|
| 9  | 4 years       | 6–11                      | HYS |
| 10 | 1 year        | 60–130 IU/L               | HYS |
| 11 | 2 year        | 17–148 IU/L (355 IU/L)[2] | Mtx, AcD |
| 12 | 1 year        | 54–500 IU/L               | Mtx, AcD |
| 13 | <½ year       | 7–35 IU/L                 | Mtx, Mtx |
| 14 | <½ year       | 12–42 IU/L                | Mtx, Mtx |
| 15 | <½ year       | 165–224 IU/L              | Mtx |
| 16 | <½ year       | 6–14                      | Mtx |
| 17 | <½ year       | 174–224 IU/L              | Mtx |
| 18 | <½ year       | 34–56 IU/L                | Mtx |
| 19 | 1 year        | 100–174 IU/L(1255 IU/L)[3]| Mtx |
| 20 | <½ year       | 10–12 IU/L                | Mtx |
| 21 | 2 year        | 50–200 IU/L               | Mtx |
| 22 | 1 year        | 2–485 IU/L                | Non-specified chemotherapy |
| 23 | <½ year       | 10–148 IU/L               | ? |
| 24 | 2 year        | 7–22 IU/L                 | ? |
| 25 | <½ year       | 157–206 IU/L              | no cancer therapy |
| 26 | <½ year       | 5–8 IU/L                  | no cancer therapy |
| 27 | 1 year        | 8–21 IU/L                 | no cancer therapy |
| 28 | 3 year        | 4–7 IU/L                  | no cancer therapy |
| 29 | <½ year       | 58–146 IU/L               | no cancer therapy |
| 30 | <1 year       | 2–10 IU/L                 | no cancer therapy |
| 31 | <1 year       | 5–10 IU/L                 | no cancer therapy |
| 32 | 2 year        | 10–40 IU/L                | no cancer therapy |
| 33 | <½ year       | 223–496 IU/L              | no cancer therapy |
| 34 | <½ year       | 6–9 IU/L                  | no cancer therapy |
| 35 | <½ year       | 6–7 IU/L                  | no cancer therapy |
| 36 | <½ year       | 14–22 IU/L                | no cancer therapy |
| 37 | 5½ year       | 23–52 IU/L                | no cancer therapy |
| 38 | <½ year       | 8–11 IU/L                 | no cancer therapy |
| 39 | <½ year       | 49–69 IU/L                | no cancer therapy |
| 40 | 1 year        | <2–20 IU/L                | no cancer therapy |

[1]After 4 years of persistent low levels of hCG (hyperglycosylated hCG not detected), values sharply rose. USA hCG Reference Service was consulted. hCG was 863 IU/L, 86% due to hyperglycosylated hCG (Table 4). Malignancy (gestational trophoblastic disease/choriocarcinoma) was demonstrated.
[2]After 2 years hCG results increased to 190 IU/ML. At that time ~100% was due to hyperglycosylated hCG (Table 4). Malignancy (PSTT) was demonstrated.
[3]After 1 year of persistent low levels of hCG (hyperglycosylated hCG not detected), values sharply rose. USA hCG Reference Service was consulted. hCG was 1255 IU/L, ~100% due to hyperglycosylated hCG (Table 4). Malignancy (gestational trophoblastic disease/choriocarcinoma) was demonstrated.

Most of the unexplained elevated hCG cases, like the false positive hCG cases, started with an incidental hCG test, ultrasound to exclude intra-uterine pregnancy, and dilation curettage and laparoscopy to exclude extra-uterine pregnancy. Patients were monitored with either no firm diagnosis or gestational trophoblastic disease was assumed. Twenty-two of the 40 (55%) cases received single agent chemotherapy, combination chemotherapy, or had a hysterectomy or other surgery (Table 5). The hCG values were not effectively abated by the therapy. A representative case is outlined in Table 6 (Table 4, case 1).

TABLE 6

| Time (days) | hCG (IU/L) | Notes |
|---|---|---|
| 0   | 44 | incidental preg test |
| 14  | 40 | D&C reveals no evidence of pregnancy |
| 21  |    | laparoscopy reveals no ectopic pregnancy |
| 72  | 52 | |
| 222 | 30 | CT/MRI scans reveal no disease |
| 240 | 32 | |
| 267 | 35 | 4 courses Mtx chemotherapy |
| 301 | 29 | |
| 322 | 35 | AcD chemotherapy |
| 420 | 34 | |
| 627 | 60 | MRI scan indicates uterine irregularities |
| 632 | 60 | HYS and BSO, pathology unremarkable |
| 642 | 34 | |
| 668 | 20 | 3 courses EMACO combination therapy |
| 803 | 24 | |
| 808 | 24 | real hCG confirmed no hyperglycosylated hCG detected, unexplained elevated hCG indicated. |

In three of the 40 cases (cases 4, 11, and 19 in Table 4), after 1, 2, and 4 years of varying low levels of hCG results (ITA was not detected), values started to sharply rise. The USA hCG Reference Service was again consulted. In one case the hCG was 190 iU/L, in the second 863 IU/L, and the third 1255 IU/L. ITA measurements were consistent with invasive/malignant disease (86%, ~100%, and ~100% of total hCG immunoreactivity). Tumor was identified by MRI/CT imaging. In the first case placental site trophoblastic tumor (PSTT) was identified by pathology and in the second and third cases gestational trophoblastic disease/choriocarcinoma was diagnosed. All three were treated with EMA-CO chemotherapy.

In summary, the USA hCG References Service observed 80 cases of persistent low levels of hCG, whether with history of hydatidiform mole or gestational trophoblastic disease (quiescent gestational trophoblastic disease) or with history of only pregnancy (unexplained elevated hCG). In 7 of the 80 cases (those referred for a second time to the USA hCG Reference Service) after periods of 2 months to 6 years of persistent low hCG levels, hCG results rapidly rose, indicating active disease. In one case PSTT was detected and in six cases gestational trophoblastic disease/choriocarcinoma was diagnosed and treated. This observation indicated that persistent low levels of hCG may be a pre-malignant condition.

Total hCG (DPC Immulite) and ITA (Nichols Institute Diagnostics: Advantage ITA test) were measured in 53 of the 80 cases with persistent low hCG levels (Tables 7 and 5). The proportion of total hCG due to ITA was determined. As shown in Table 4, ITA was not detected (<2 IU/L) in 49 of the 53 cases with persistent low levels of hCG, and accounted for no more than 21% (<30%) of the total hCG in the remaining four cases. Sera from 13 additional patients with proven choriocarcinoma were also examined. In all cases, only high proportions of ITA (>30% of total hCG) were detected (Table 4).

As described in Tables 7 and 3, in 7 of the 80 cases with persistent low levels of hCG, malignant disease developed. ITA results were 57% to 100% of total hCG (Table 4). Putting these cases together, ITA accounted for more than 30% of total hCG immunoreactivity in 20 of 20 malignant cases, and in none of the 53 individuals with persistent elevated hCG (non-invasive disease). The data indicated that the percent ITA is an accurate indicator of invasive/malignant trophoblastic disease, with use in differentiating persistent low levels of hCG from malignant disease.

TABLE 7

| Case | Treatment given because of persistent false positive hCG result | False hCG result recorded by physician at time of hCG Reference Service testing |
|---|---|---|
| 1 | D&C, Lap, Mtx, AcD, HYS, EMACO, THO | 220 IU/L hCG |
| 2 | D&C, Lap, Mtx, HYS, EMACO, Coma | 68 IU/L hCG |
| 3 | D&C, Lap, Mtx, Mtx, AcD, HYS | 142 IU/L hCG |
| 4 | D&C, Lap, Mtx, HYS | 17 IU/L hCG |
| 5 | D&C, Lap, HYS, BSO | 150 IU/L hCG |
| 6 | D&C, Lap, Mtx, BSO | 145 IU/L hCG |
| 7 | D&C, Lap, Mtx, HYS, BSO | 81 IU/L hCG |
| 8 | D&C, Lap, Mtx, AcD, EMACO | 558 IU/L hCG |
| 9 | D&C, Lap, Mtx, EMACO | 80 IU/L hCG |
| 10 | D&C, Lap, Mtx, AcD | 22 IU/L hCG |
| 11 | D&C, Lap, Mtx, AcD | 21 IU/L hCG |
| 12 | D&C, Lap, Mtx, AcD | 110 IU/L hCG |
| 13 | D&C, Lap, Mtx, AcD | 114 IU/L hCG |
| 14 | D&C, Mtx, D&C, Lap, Mtx | 24 IU/L hCG |
| 15 | D&C, Lap, Mtx, Mtx | 97 IU/L hCG |
| 16 | D&C, D&C, Lap, Mtx | 122 IU/L hCG |
| 17 | D&C, Mtx, ActD | 14 IU/L hCG |
| 18 | D&C, Lap, Mtx | 60 IU/L hCG |
| 19 | D&C, Lap, Mtx | 32 IU/L hCG |
| 20 | D&C, Lap, Mtx | 402 IU/L hCG |
| 21 | D&C, Lap, Mtx | 37 IU/L hCG |
| 22 | D&C, Lap, Mtx | 607 IU/L hCG |
| 23 | D&C, Lap, Mtx | 300 IU/L hCG |
| 24 | D&C, Lap, Mtx | 170 IU/L hCG |
| 25 | D&C, Lap, Mtx | 21 IU/L hCG |
| 26 | D&C, Mtx | 20 IU/L hCG |
| 27 | D&C, Mtx | 202 IU/L hCG |
| 28 | D&C, Mtx | 18 IU/L hCG |
| 29 | D&C, Mtx | 23 IU/L hCG |
| 30 | D&C, Mtx | 81 IU/L hCG |
| 31 | D&C, Mtx | 32 IU/L hCG |
| 32 | D&C, Mtx | 170 IU/L hCG |
| 33 | D&C, Mtx | 12 IU/L hCG |
| 34 | D&C, Mtx | 124 IU/L hCG |
| 35 | D&C, Mtx | 70 IU/L hCG |
| 36 | D&C, Mtx | 21 IU/L hCG |
| 37 | D&C, Mtx | 17 IU/L hCG |
| 38 | D&C, Lap | 14 IU/L hCG |
| 39 | D&C, Lap | 23 IU/L hCG |
| 40 | D&C, Lap | 24 IU/L hCG |
| 41 | D&C, Lap | 53 IU/L hCG |
| 42 | D&C | 32 IU/L hCG |
| 43 | D&C | 93 IU/L hCG |
| 44 | D&C | 143 IU/L hCG |
| 45 | — | 25 IU/L hCG |
| 46 | — | 18 IU/L hCG |
| 47 | — | 7 IU/L hCG |
| 48 | — | 224 IU/L hCG |
| 49 | — | 20 IU/L hCG |
| 50 | — | 18 IU/L hCG |
| 51 | — | 25 IU/L hCG |
| 52 | Male patient, testicular cancer considered | 38 IU/L hCG |

Example 3

Presence of ITA in Germ Cell Cancers

Three patients suspected of having seminoma or testicular choriocarcinoma, both of which are testicular germ cell cancers, were referred to the USA hCG Reference Service. Samples of urine and serum were obtained from each patient and the level of total hCG was analyzed using DPC Immulite test kit. The samples were then tested for immunoreactivity to ITA using the Nichols Institute Diagnostics: Advantage ITA test. In all three cases, all of the hCG immunoreactivity was due to ITA, showing that these testicular germ cell cancers, like placenta choriocarcinoma, produce ITA.

In addition, five patients diagnosed as having ovarian germ cell malignancies (dysgerminoma) were referred to the hCG Reference Service. Samples from these five patients were also analyzed for total hCG titers (DPC Immulite), followed by testing for ITA immunoreactivity (Nichols Institute Diagnostics: Advantage ITA test). All of the hCG immunoreactivity in these patients was due to ITA. Thus, ITA serves as a useful marker to detect both testicular and ovarian germ cell cancers.

REFERENCES CITED IN THE EXAMPLES

1. Cole L A. Phantom hCG and phantom choriocarcinoma. Gynecol Oncol 1998; 71:325-329.
2. Rotmensch S, Cole L A. False diagnosis and needless therapy of presumed malignant disease in women with false-positive human chorionic gonadotropin concentrations. Lancet 2000; 355:712-715.
3. Cole L A, Shahabi S, Butler S, Mitchell H, Newlands E, Behrman H R, Verrill H L. Utility of commonly used commercial hCG immunoassays in the diagnosis and management of trophoblastic diseases. Clin Chem 2001; 47:308-315.
4. Cole L A, Butler SA. False positive or phantom hCG result: a serious problem. Clin Lab Intl 2001; 25:9-14.
5. Cole L A, Butler S A. Detection of hCG in Trophoblastic Disease: The USA hCG Reference Service experience. J Reprod Med 2002; 47:433-444.
6. Butler S A, Cole L A. The Use of heterophilic antibody blocking agent (HBT) in reducing false positive hCG results. Clin Chem 2001; 47:1332-1333.

7. Butler S A, Cole L A. Falsely elevated hCG leading to unnecessary therapy (letter). Obstet Gynecol 99:515-516, 2002.
8. Cole L A, Shahabi S, Oz U A, Bahado-Singh R O, Mahoney M J. Hyperglycosylated hCG (invasive trophoblast antigen) immunoassay: a new basis for gestational down syndrome screening. Clin Chem 1999; 45:2109-2119.
9. Suzuki T, Goto S, Nawa A, Kurauchi O, Saito M, Tomoda Y. Identification of the pregnancy responsible for gestational trophoblastic disease by DNA analysis. Obstet Gynecol 1993:82, 629-34.
10. Kohom E I. Persistent low-level 'real' human chorionic gonadotropin: a clinical challenge and a therapeutic dilemma. Gynecol Oncol 2002; 85:315-320.
11. Newlands E S. Presentation and management of persistent gestational trophoblastic disease and gestational trophoblastic tumors in the UK. In: Hancock B W, Newland E S, Berkowitz R S, editors. Gestational Trophoblastic Disease. London: Chapman and Hall; 1997. p. 143-156.
12. Berkowitz R S, Goldstein D P. Presentation and management of molar pregnancy. In: Hancock B W, Newland E S, Berkowitz R S, editors. Gestational Trophoblastic Disease. London: Chapman and Hall; 1997. p. 127-142.
13. O'Connor J F, Ellish N, Kakuma T, Schlatterer J, Kovalevskaya G. Differential urinary gonadotrophin profiles in early pregnancy and early pregnancy loss. Prenat Diagn 1998; 18:1232-1240.
14. Elliott M M, Kardana A, Lustbader J W, Cole L A. Carbohydrate and peptide structure of the α- and β-subunits of human chorionic gonadotropin from normal and aberrant pregnancy and choriocarcinoma. Endocrine 7, 15-32, 1997.

The preceding examples can be repeated with similar success by substituting the generically or specifically described reactants and/or operating conditions of this invention for those used in the preceding examples.

It should be understood that the foregoing disclosure emphasizes certain specific embodiments of the invention and that all modifications or alternatives equivalent thereto are within the spirit and scope of the invention as set forth in the appended claims.

I claim:

1. A method of detecting the presence or absence of invasive trophoblast cells in a patient risk for gestational trophoblastic disease or having a germ cell tumor comprising the steps of:
   a. obtaining a urine, saliva, serum or plasma sample from said patient;
   b. determining the amount of hCG in the sample wherein the amount of hCG comprises the total amount of intact hCG and ITA in the sample or comprises the total amount of intact hCG plus the amount of free β subunit of hCG and ITA in the sample;
   c. determining the total amount of ITA in the sample in an immunoassay which determines the selective binding of monoclonal B152 to ITA;
   d. determining the percentage of the amount of hCG determined in step b that is ITA, and
   e. determining that invasive trophoblast calls are present in the patient if the percentage of the amount of HCG that is ITA determined in step d is 30% or greater such that a diagnosis of gestational trophoblastic disease or the existence of a germ cell tumor may be made, wherein the amount of hCG comprises the total amount of intact hCG and ITA, plus the amount of free β sub unit of hCG in the sample.

2. The method of claim 1, wherein the patient is a woman previously diagnosed as having a gestational trophoblastic disease.

3. The method of claim 2, wherein the gestational trophoblastic disease is hydatidiform mole.

4. The method of claim 2, wherein the gestational trophoblastic disease is choriocarcinoma.

5. The method of claim 2, wherein the gestational trophoblastic disease is placenta-site trophoblastic tumor.

6. The method of claim 1, wherein the biological sample is urine, plasma or serum.

7. The method of claim 6 wherein the biological sample is urine.

8. A method of diagnosing quiescent gestational trophoblastic disease in a patient previously diagnosed as having quiescent gestational trophoblastic disease or previously diagnosed as having a gestational trophoblastic disease comprising the steps of:
   a. obtaining a urine, saliva, serum or plasma sample from said patient, wherein said patient has persistently low hCG titers;
   b. determining the amount of hCG in the sample wherein the amount of hCG comprises the total amount of intact hCG plus ITA in the sample or comprises the total amount of intact hCG plus ITA plus the amount of free β subunit of hCG in the sample;
   c. determining the total amount of ITA in the sample in an immunoassay which determines the selective binding of monoclonal B152 to ITA;
   d. determining the percentage of the amount of hCG from step b that is ITA, and
   e. diagnosing quiescent gestational trophoblastic disease in said patient if the percentage of total hCG that is ITA determined in step (d) is less than 30%.

9. The method of claim 8, wherein the patient is a woman previously diagnosed as having a gestational trophoblastic disease.

10. The method of claim 9, wherein the gestational trophoblastic disease is hydatidiform mole.

11. The method of claim 9, wherein the gestational trophoblastic disease is choriocarcinoma.

12. The method of claim 9, wherein the gestational trophoblastic disease is placenta-site trophoblastic disease.

13. The method of claim 8, wherein the amount of hCG comprises intact hCG, ITA and the free β subunit of hCG.

* * * * *